US 6,554,800 B1

(12) United States Patent
Nezhadian et al.

(10) Patent No.: US 6,554,800 B1
(45) Date of Patent: Apr. 29, 2003

(54) COMPACT PUMP MOTOR SYSTEM AND DISPENSING PROCESS

(75) Inventors: Hiwa Nezhadian, Simi Valley, CA (US); Rolf O. Orchard, Manhattan Beach, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 29 days.

(21) Appl. No.: 09/636,083

(22) Filed: Aug. 9, 2000

(51) Int. Cl.[7] ............................. A61M 1/00; F04B 17/04
(52) U.S. Cl. ...................... 604/152; 310/23; 335/228; 417/416
(58) Field of Search ............................. 335/228, 255; 310/23; 604/152; 417/416

(56) References Cited

U.S. PATENT DOCUMENTS

| | | | |
|---|---|---|---|
| 3,618,868 A | 11/1971 | Bohuslav Vavrinec | 242/4 |
| 4,562,751 A | 1/1986 | Nason et al. | 74/111 |
| 4,678,408 A | 7/1987 | Nason et al. | 417/410 |
| 4,685,903 A | 8/1987 | Cable et al. | 604/154 |
| 5,080,653 A | 1/1992 | Voss et al. | 604/152 |
| 5,097,122 A | 3/1992 | Colman et al. | 604/151 X |
| 5,318,521 A * | 6/1994 | Slettenmark | 604/152 X |
| 5,687,698 A * | 11/1997 | Mastro et al. | 335/255 X |
| 6,086,042 A * | 7/2000 | Scott et al. | 335/255 X |

* cited by examiner

Primary Examiner—William Wayner
(74) Attorney, Agent, or Firm—Medtronic MiniMed, Inc.

(57) ABSTRACT

A drive motor for an infusion pump system includes a novel outer housing which includes a unitary member which defines a cavity adapted to receive a winding wherein the housing cavity has a length at least as long as length of the winding. In one embodiment, the housing unitary member has an opening at one end and is adapted to receive a housing end member which has a guide track for an armature. Such an arrangement facilitates assembly and disassembly of the motor for fabrication, inspection and repair purposes yet also facilitates proper alignment of the components when assembled. In another aspect, a push member positioned to be engaged by the armature has an engagement face which is at least 40% of the width of the armature engagement face. In still another aspect of the present inventions, the armature head portion is wider than the armature stem portion and has a length at least 10% of the winding length. In yet another aspect of the present inventions the push member may have a single diameter cylindrical shape and the push member guide track similarly may have a single diameter cylindrical shape which is sized to slidingly receive the push member. It is believed that one or more of these features can increase the actuation force provided by the motor yet maintain a compact size.

31 Claims, 6 Drawing Sheets

COMPACT PUMP MOTOR SYSTEM AND DISPENSING PROCESS

BACKGROUND OF THE INVENTION

1. Field of the Invention

This invention relates generally to improvements in infusion pumps such as those used for controlled delivery of medication to a patient. More specifically, this invention relates to an improved motor system for infusion pumps and to improved medication delivery.

2. Description of the Related Art

Infusion pump devices and systems are relatively well-known in the medical arts, for use in delivering or dispensing a prescribed fluid medication such as insulin to a patient. In one form, such devices comprise a relatively compact pump housing adapted to receive a syringe or reservoir carrying a prescribed fluid medication for administration to the patient through infusion tubing and an associated catheter or infusion set.

The infusion pump includes a small drive motor connected via a suitable transmission such as a lead screw assembly to advance a reservoir piston to administer the medication to the user. Programmable controls can operate the drive motor continuously or at periodic intervals to obtain a closely controlled and accurate delivery of the fluid medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above can provide significant advantages and benefits with respect to accurate delivery of medication or other fluids over an extended period of time. However, the infusion pump should also be designed to be compact, and readily carried by the user by means of a belt clip or the like. If so, important medication can be delivered to the user not only with precision and in an automated manner, but also with reduced restriction on the user's mobility and life-style.

SUMMARY OF THE PREFERRED EMBODIMENTS

In accordance with one aspect of the inventions, a drive motor for an infusion pump system includes a novel outer housing which includes a unitary member which defines a cavity adapted to receive a winding wherein the housing cavity has a length at least as long as a length of the winding. In the illustrated embodiment, the housing unitary member has an opening at one end adapted to receive a housing end member which has a guide track for an armature. The guide track of the housing end member extends at least partially into a magnetic field generation area of the winding. An armature is slidingly received in the housing end member guide track, and is adapted to slide along the housing end member guide track in response to a magnetic field generated in the magnetic field generation area. As explained in greater detail below, such an arrangement facilitates assembly and disassembly of the motor for fabrication, inspection and repair purposes yet also facilitates proper alignment of the components when assembled.

In the illustrated embodiment, the housing defines a push member guide track aligned with the end armature guide track. The drive motor has a push member slidingly received in the push member guide track and is positioned to be engaged by the armature and to slide along the push member guide track in response to engagement by the armature. In accordance with another aspect of the present inventions, the push member has an engagement face which is at least 40% of the width of the armature engagement face. In still another aspect of the present inventions, the armature may have a stem portion which is slidingly received in the armature guide track and a head portion positioned to engage the push member wherein the armature head portion is wider than the armature stem portion and has a length at least 10% of the winding length. In yet another aspect of the present inventions, the push member may have a single diameter cylindrical shape and the push member guide track may similarly have a single diameter cylindrical shape which is sized to slidingly receive the push member. It is believed that one or more of these features can increase the actuation force provided by the motor yet maintain a compact size.

There are additional aspects to the present inventions as discussed below. It should therefore be understood that the preceding is merely a brief summary of some embodiments of the present inventions. It should further be understood that numerous changes to the disclosed embodiments can be made without departing from the spirit or scope of the inventions. The preceding summary, therefore is not meant to limit the scope of the inventions. Rather, the scope of the inventions is to be determined only by the appended claims and their equivalents.

DETAILED DESCRIPTION OF THE DRAWINGS

Figure 1:
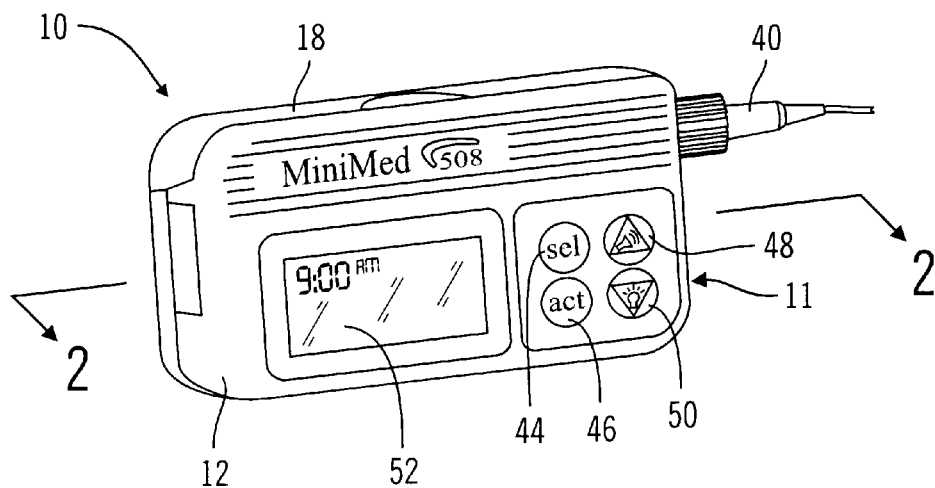
FIG. 1 is a perspective view of an infusion pump system in accordance with one embodiment of the present invention.
Figure 2:
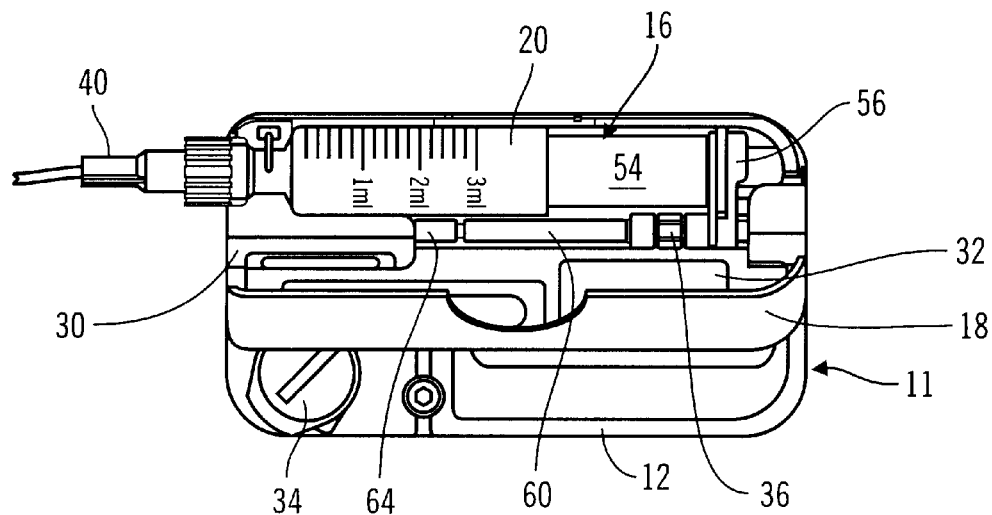
FIG. 2 is a rear view of the pump of FIG. 1 with a syringe door shown in an open position.

An infusion pump system in accordance with one embodiment of the present inventions is indicated generally at 10 in FIGS. 1 and 2. The infusion pump system 10 includes an infusion pump 11 having an outer casing or housing 12 which houses a dispenser 16. The housing 12 has a rear door 18 which may be pivoted open (FIG. 2) to provide access to the interior of the pump 11. The dispenser 16 includes a fluid reservoir 20 which contains a fluid medication to be dispensed to the user. When the reservoir becomes sufficiently empty, the housing door 18 may be opened to remove the old dispenser and to install a new dispenser with a fresh supply medication in it reservoir.

Also disposed within the housing 12 is a motor drive assembly 30 (FIG. 2) and a control circuit 32 which control s the operation of the motor drive assembly 30 to dispense the fluid medication from the reservoir 20. As will be explained in greater detail below, the motor of the motor drive assembly, in one aspect of the illustrated embodiments, is designed to facilitate assembly and disassembly of the motor for fabrication, inspection and repair purposes yet also facilitate proper alignment of the components when assembled. In addition, in one embodiment, the number of parts may be reduced as compared to prior designs.

The motor drive assembly 30 is powered by a power source, which in the illustrated embodiment, includes a battery 34 housed within the housing 12. The control circuit 32 includes suitable power generation circuitry coupled to the output of the battery 34 to provide appropriate power levels to drive the motor drive assembly 30. A transmission 36 mechanically couples the motor drive assembly 30 to the dispenser 16 to pump the fluid medication from the reservoir 20 of the dispenser 16. The fluid medication is output from the reservoir 20 through a conduit 40 which is connected to a catheter or subcutaneous insertion point for input to the user. A plurality of user operable buttons including a button 44 labeled "sel"; a button 46 labeled "act"; an up arrow button 48; and a down arrow button 50 are disposed through housing 12 and may be used to program the control circuit 32 or to display certain information on a display 52 which, in the illustrated embodiment is an LCD.

In the illustrated embodiment, the dispenser 16 has a plunger 54 (FIG. 2) which when driven forward into the reservoir 20, forces the fluid medication from the fluid reservoir 20 and through the conduit 40 to the user. The end of the plunger is engaged by a pump driver member 56 which is incrementally driven forward by the transmission 36. In the illustrated embodiment, the transmission 36 is a lead screw type transmission and includes a lead screw 60 coupled by a coupler 64 to a drive shaft 68 (FIG. 3) of the motor drive assembly 30. The lead screw 60 of the transmission 36 is rotated by the drive shaft 68 which in turn is rotated by a ratchet wheel 70 of the motor drive assembly 30 as explained in greater detail below. In the illustrated embodiment, rotation of the lead screw 60 in a clockwise direction causes the pump driver member 56 to move toward the reservoir 20. In this manner, the pump driver member 56 causes the plunger 54 to be driven into the reservoir 20, thereby forcing fluid from the reservoir into conduit 40.

Figure 3:
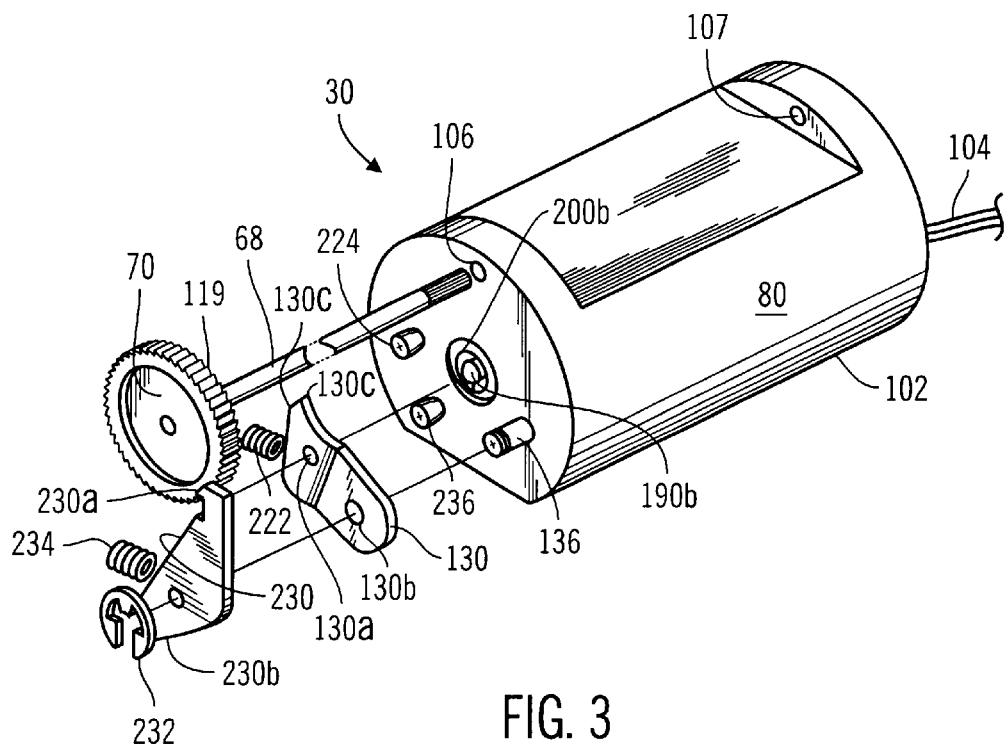
FIG. 3 is a partially exploded perspective view of the motor drive assembly of the pump of FIG. 2.
Figure 4:
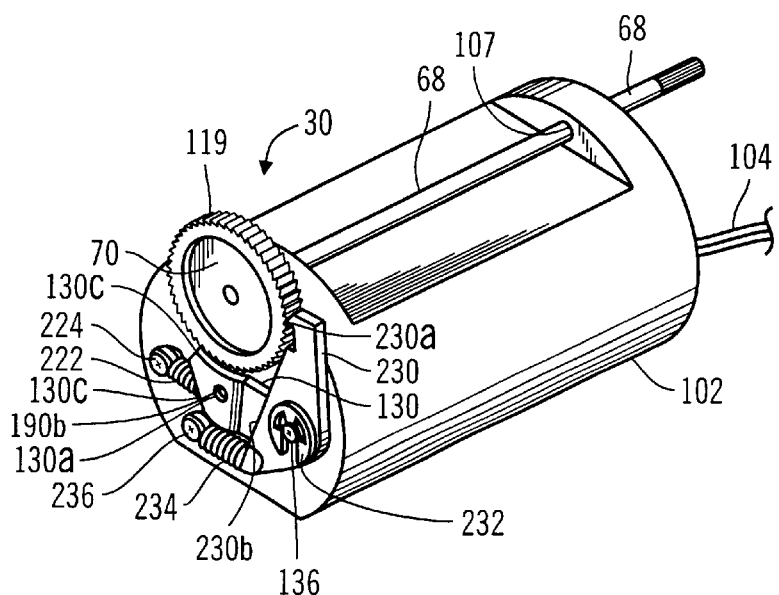
FIG. 4 is an assembled perspective view of the motor drive assembly of FIG. 3.
Figure 5:
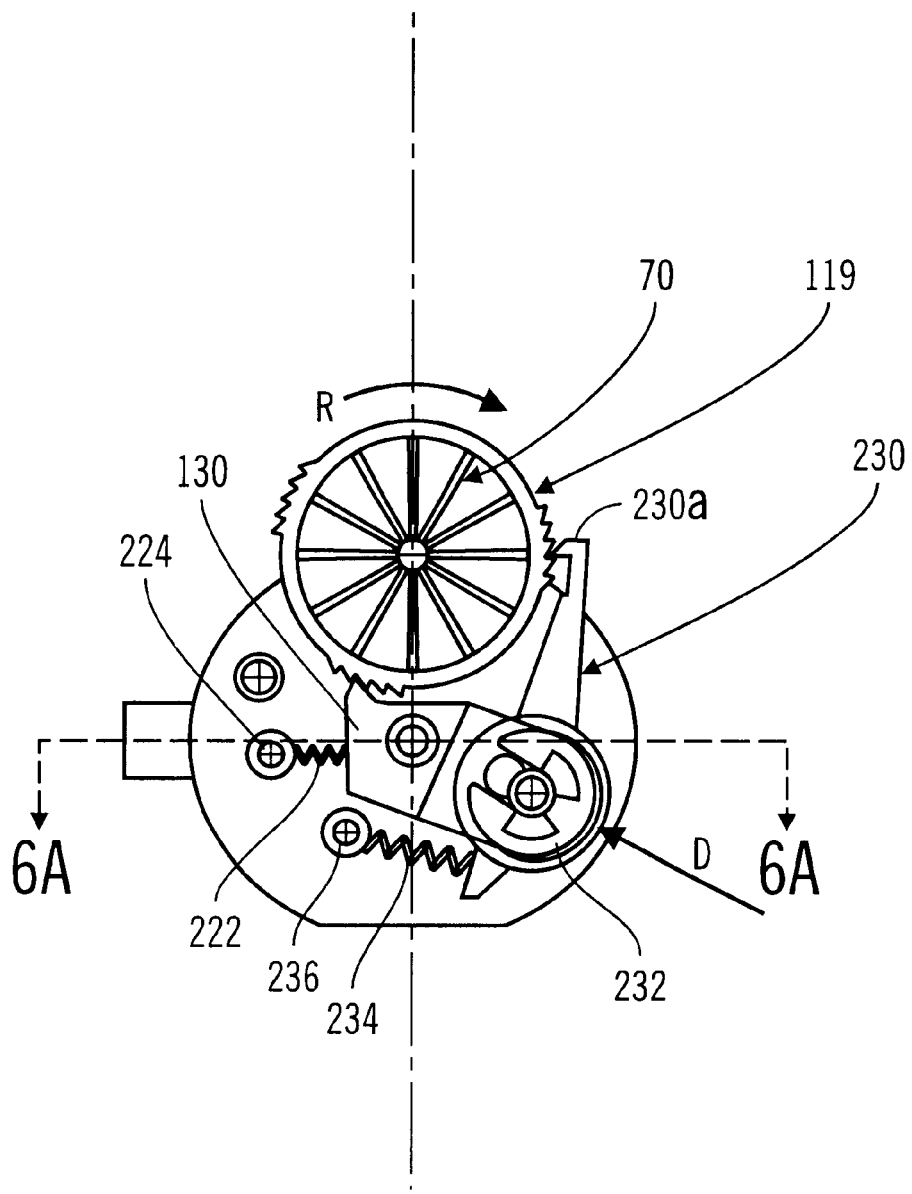
FIG. 5 is an end view of the motor drive assembly of FIG. 4.

The motor drive assembly 30 is shown in greater detail in FIGS. 3–5. In the illustrated embodiment, the motor drive assembly 30 includes a motor 80 which is a solenoid type motor which converts electrical energy into mechanical energy, first in the form of linear motion, and then in the form of rotational or angular motion. The motor 80 of the motor drive assembly 30 has an outer housing 102 and leads 104 for receiving the output from the power generation circuit of the control circuit 32 (FIG. 1). The housing also has bores 106 and 107 for receiving there through the drive shaft 68 for driving the lead screw 60 through the coupling 54 (FIG. 1). Attached to the other end of the drive shaft 68 is the ratchet wheel 70 having teeth 119 disposed around the periphery. As explained in greater detail below, a pawl 130 slidingly mounted on a post 136 and driven by the motor 80, engages the teeth 119 of the ratchet wheel 70 to cause the ratchet wheel 70 to rotate.

Figure 6A:
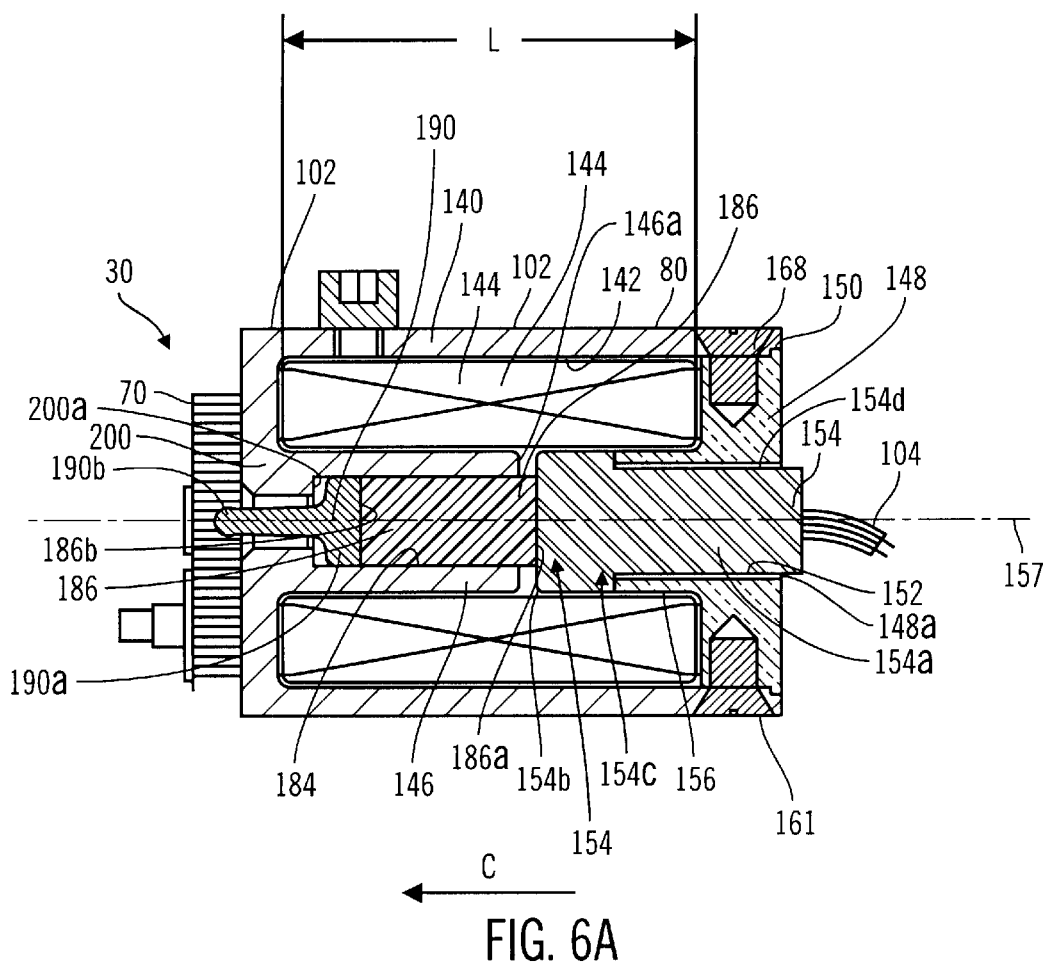
FIG. 6A is a cross-sectional view of the motor drive assembly of FIG. 5 as viewed along the line 6A—6A of FIG. 5, showing the motor in the rest position.
Figure 6B:
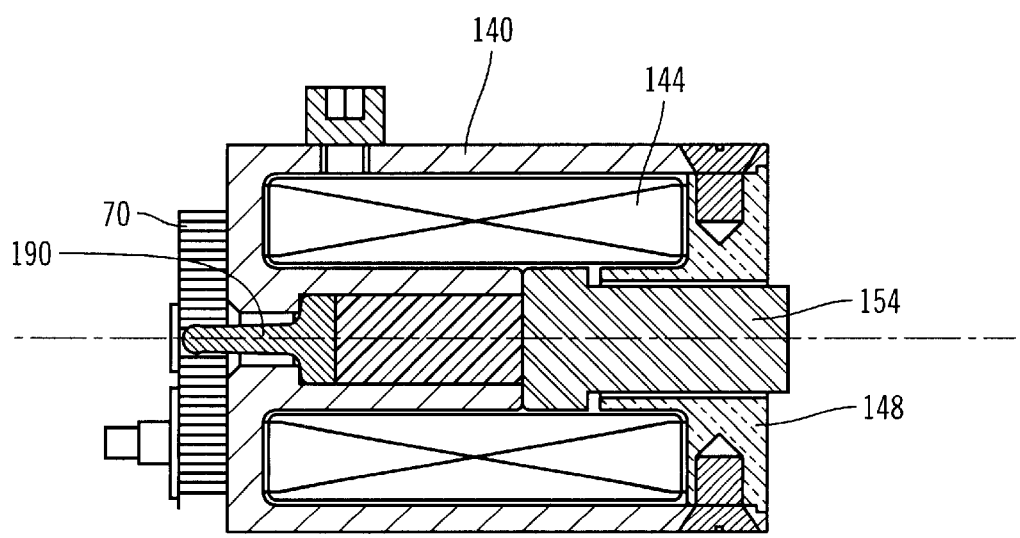
FIG. 6B is a cross-sectional view of the motor drive assembly of FIG. 5 as viewed along the line 6A—6A of FIG. 5, showing the motor in the energized position.

As best seen in FIGS. 6A and 6B, the housing 102 of the motor 80 includes a generally cylindrical cavity member 140 which defines a generally annular shaped interior cavity 142. An annular-shaped solenoid winding 144 is disposed in the cavity 142 around a central core portion 146 of the cavity member 140. In the illustrated embodiment, the cavity member 140 is formed as a unitary or one-piece member of a magnetically permeable material such as stainless steel and has a sufficient length such that the cavity 142 of the cavity member 140 extends at least the length L of the winding 144 as shown in FIGS. 6A and 6B. In the illustrated embodiment, the winding 144 has a length of approximately 0.54 inches (13.7 mm) and the cavity 142 of the cavity member 140 extends approximately 0.65 inches (16.5 mm). Of course, the material and dimensions of the various components of the drive motor may vary, depending upon the particular application.

The motor housing 102 further includes an end cap member 148 received in an opening 150 (FIG. 7) at the open end of the cavity 142 of the cavity member 140. In the illustrated embodiment, the thickness of the end cap member 148 adjacent the cavity member 140 is approximately 0.1 inches (2.5 mm), leaving approximately 0.55 inches (14.0 mm) of cavity 142 within the cavity member 140 for the winding 144.

The end cap member 148 defines a guide track 152 upon which an armature 154 slides. In the illustrated embodiment, the guide track 152 is formed by a cylindrical bore formed in a central core portion 156 of the end cap member 148. The armature 154 has a correspondingly generally cylindrically shaped stem portion 154a slidingly received in the bore 152 of the end cap member 148, and is formed of a magnetically permeable material such as stainless steel. Examples of suitable stainless steel for the armature 154 and the cavity member 140 include stainless steel 430 FR or chrome core. In order to reduce friction between the cylindrical engagement surface of the guide track 152 and the outer cylindrical engagement surface 154d of the stem portion 154a of the armature 154, the surface roughness of the guide track engagement surface 152 and the armature stem portion outer engagement surface 154d is preferably less than 16 microns and more preferably in a range of 8–12 microns. Such an arrangement is believed to increase the net force applied by the armature when actuated.

The bore-shaped guide track 152 and the armature 154 slidingly carried by the guide track 152 are aligned with the center axis 157 of the winding 144 and extend into the hollow interior of the winding 144. The armature 154 is positioned within the magnetic field generated by the winding 144 when the winding is energized. FIG. 6A represents the position of the armature 154 in a "rest" position prior to energizing the winding 144. When the winding 144 is energized, the armature is drawn in a direction indicated at C, further into the interior of the winding 144, by the magnetic attraction exerted by the field generated by the winding 144 to an "energized" or "actuated" position as shown in FIG. 6B.

Figure 7:
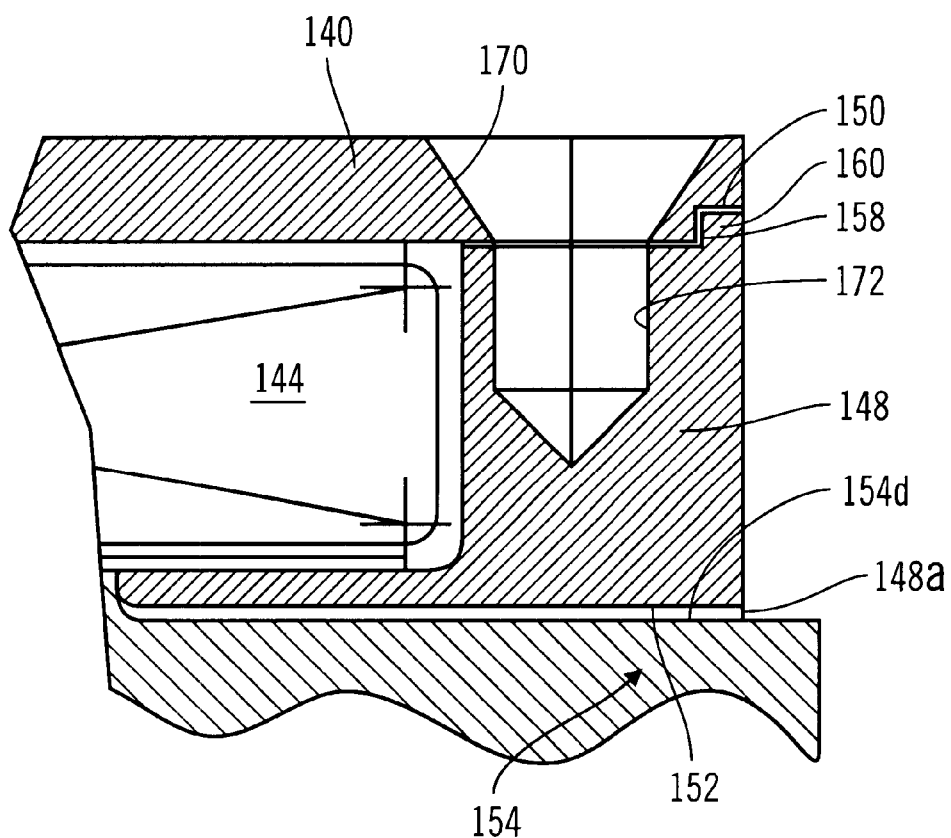
FIG. 7 is an enlarged partial view of the cross-sectional view of the end cap of FIG. 6A.

As best seen in FIG. 7, the opening 150 of the cavity member 140 includes a shoulder 158 which receives a flange 160 of the end cap member 148. The flange 160 of the end cap member 148 is sized slightly smaller than the size of the shoulder 158 of the opening 150 of the cavity member 140 to facilitate aligning the end cap member 148 relative to the cavity member 140. Because the cavity member 140 and the end cap member 148 are each formed separately of unitary construction, alignment of the end cap member guide track 152 relative to the winding 144 of the cavity member 140 is also readily achieved. In addition, the end cap member 148 is readily fastened to the cavity member 140 by screws 168 which pass through screw openings 170 at the end of the cavity member 140 and are threaded into threaded bores 172 positioned in the end cap member 148. Such an arrangement facilitates both assembly and disassembly of the motor housing 102 for fabrication, inspection and repair purposes. Previously, housing components have been welded together, thereby making disassembly for inspection or repair purposes more difficult if not all together prevented. It should be appreciated that other types of releasable fasteners may be used. For example, the end cap member 148 may be threaded into the opening 150 of the cavity member 140. Also, retaining rings, dowel pins, C-clips and wire clips are additional examples of suitable fasteners as explained in greater detail below.

Referring again to FIGS. 6A and 6B, the central core portion 146 of the cavity member 140 further defines a second guide track 184 which slidingly receives a push member 186 in the form of a single diameter, cylindrically shaped rod. The guide track 184 is correspondingly bore-shaped and has a single interior diameter sized to slidingly receive the push rod 186. Such an arrangement is believed to facilitate smooth sliding between the core portion guide track 184 and the push rod 186. The push rod 186 is preferably made from a light-weight nonmagnetic material such as plastic. Examples of suitable materials include Torlon (such as, for example Torlon 4203), Peek or Delrin.

When the winding 144 is energized, a disk-shaped engagement face 154*b* of a cylindrically shaped head portion 154*c* of the armature 154, engages a disk-shaped engagement face 186*a* of the push rod 186. Because the push rod 186 is formed of a nonmagnetic material in the illustrated embodiment, the push rod is not responsive to the magnetic field generated when the winding 144 is energized. As a consequence, the push rod 186 does not exert an opposing force to the armature when the winding is energized.

The width of the engagement face 186*a* of the push rod 186 is preferably at least 40% of the width of the engagement face 154*b* of the armature 154. In the illustrated embodiment, the area of the engagement face 186*a* of the push rod 186 is approximately 41% of the area of the engagement face 154*b* of the armature 154. The head portion 154*c* of the armature 154 is preferably at least 20% wider than the stem portion 154*a* and has a length which is preferably at least 10% of the length of the winding 144. In the illustrated embodiment, the head portion 154*c* has a length which is preferably in the range of 0.80 to 0.125 inches (2.03 to 3.17 mm), and more preferably 0.100 inches (2.54 mm).

In the illustrated embodiment, the cross-sectional area of the head portion 154*c* of the armature 154 is preferably between 35% and 63%, and more preferably is 45% larger than the cross-sectional area of the stem portion 154*a*. The overall length of the armature 154 is preferably greater than 0.300 inches (7.6 mm) and more preferably is 0.350 inches (approximately 8.9 mm) which is approximately 65% of the length of the winding 144. In the illustrated embodiment, the guide track 152 of the end cap 148 extends to an aperture 148*a* of the end cap such that one end 154*e* of the armature 154 extends outside the end cap 148. It is believed that one or more of the above features of the end cap, push rod and armature can increase the actuation force provided by the motor yet maintain a compact size.

When the winding 144 is energized, drawing the armature 154 in the direction C, the armature engages the push rod 186 and drives the push rod 186 to the energized position shown in FIG. 6B. The end 146*a* of the central core portion 146 provides a stop surface for the armature at the end of the travel of the armature in the energized position.

The push rod 186 has a second engagement face 186*b* which is aligned with a pawn 190 positioned at the end of the cavity member guide track 184. The pawn 190 has a base 190*a* and a tip 190*b* and is adapted to rock in a rocking motion between a "rest" position as shown in FIG. 6A and an actuated position as shown in FIG. 6B. When the winding 144 is not energized, the pawn 190 is in the rest position in which the pawn tip 190*b* is out of alignment with the central axis 157 of the cavity member guide track 184 as shown in FIG. 6A. When the winding 144 is energized, the pawn 190 moves to the actuated position in which the pawn tip 190*b* pivots into alignment with the central axis 157 of the cavity member guide track 184 as shown in FIG. 6B. The pawn 190 is pivoted to the actuated position by the push rod engagement face 186*b* engaging the base 190*a* of the pawn 190 and pushing the pawn 190 along the cavity member guide track 184 until the base 190*a* of the pawn 190 engages a stop surface 200*a* of a bushing portion 200. In the illustrated embodiment, the bushing portion is preferably integrally formed as a portion of the central core portion 146 of the cavity member 140 to facilitate assembly of the drive motor 80.

As best seen in FIG. 3, the tip 190*b* of the pawn 190 extends through an aperture 200*b* of the bushing portion 200 to the exterior of the drive motor housing 102. The pawn tip 190*b* further extends into an aperture 130*a* of the pawl 130. The pawl 130 mounted on the post 136 includes a slot 130*b* which receives the post 136 and permits linear movement of the pawl 130. When the winding 144 is energized, rocking the pawn 190 to the actuated position of FIG. 6B, the pawn tip 190*b* engages the pawl aperture 130*a* and drives the pawl 130 in the direction D as indicated in FIG. 5. A tip 130*c* of the pawl 130 driven by the pawn 190 of the motor 80, engages the teeth 119 of the ratchet wheel 70 to cause the ratchet wheel 70 to rotate an incremental movement in direction R. As previously mentioned, rotation of the ratchet wheel 70 rotates the lead screw 60 of the transmission 36. In the illustrated embodiment, rotation of the lead screw 60 in a clockwise direction causes the pump driver member 56 to move toward the reservoir 20. In this manner, the pump driver member 56 causes the plunger 54 to be driven into the reservoir 20, thereby forcing medication fluid from the reservoir into conduit 40 to the user.

As the pawn 190 rocks to its actuated position, a spring 222 positioned between a housing post 224 and the pawn 190, will be biased by the pawn movement. When the charge to the solenoid winding 144 is depleted, the spring 222 will force the pawl 130 and the pawn 190 back to their original positions. In addition, as the ratchet wheel 70 rotates in the direction R, a tip 230*a* of an "antibacklash" pawl 230 is lifted over a tooth of the ratchet wheel 70. The pawl 230 is rotatably mounted on the same housing post 136 as the pawl 130. An E-ring 232 is disposed on the end of post 136 to hold pawls 130 and 230 in place when the apparatus is assembled. A second spring 234 positioned between a housing post 236 and an end 230*b* of the pawl 230, is compressed by the lifting of the pawl tip 230*a*. The spring 234 then extends and pivots the pawl 230 back to its original position. However the pawl tip 230*a* will be positioned against the next tooth of ratchet wheel 70. In this manner, the ratchet wheel ratchets forward (in the direction R) and rotation of the ratchet wheel 70 backwards (opposite of direction R) is limited by the antibacklash pawl 230 to half the distance between adjacent teeth. This ratcheting action will take place each time the charge is delivered from the power supply circuit to the solenoid windings.

Figure 8:
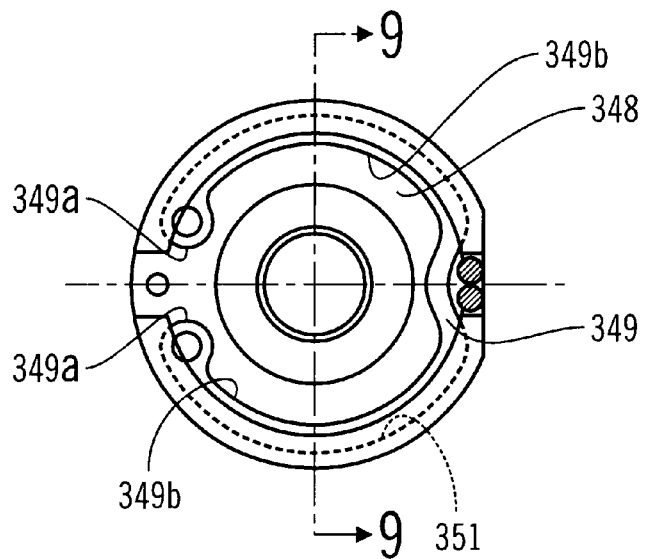
FIG. 8 is an end view of a motor housing in accordance with an alternative embodiment.
Figure 9:
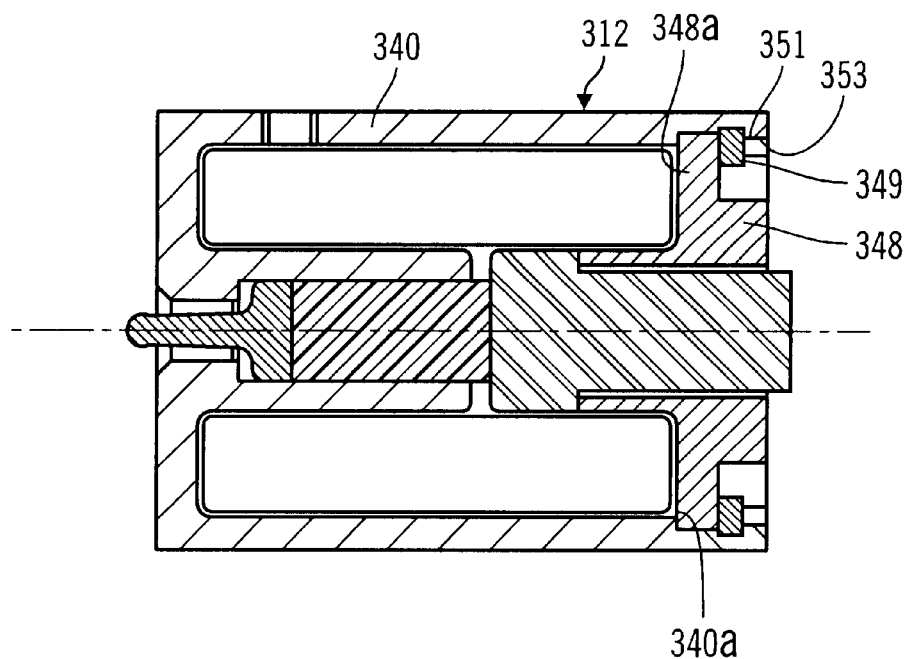
FIG. 9 is a cross-sectional view of the motor housing of FIG. 8 viewed along the line 9—9 of FIG. 8.

Referring now to FIGS. 8 and 9, a motor housing in accordance with an alternative embodiment is indicated generally at 312. The housing 312 includes a unitary housing cavity member 340 and an end cap member 348 which are generally similar to the corresponding cavity member 140 and end cap member 148 of the embodiment of FIGS. 6A and 6B. However, rather than utilizing screw fasteners to fasten the end cap member 348 to the cavity member 340, the motor housing 312 has a rotor spring clip 349 received in a groove received in a groove 351 adjacent an opening 353 at the end of the cavity member 340. The end cap member 348 has a flange 348a which abuts a shoulder 340a of the cavity member on one side of the flange 348a. The spring clip 349 engages the opposite side of the end cap flange 348a to secure the end cap member 348 in the opening 353 of the cavity member 340.

To assist in removing or installing the rotor spring clip 349, the clip 349 has a pair of rings 349a disposed at each end of a pair of resilient legs 349b. Ends of a needle nose pliers may be inserted into the rings 349a and by closing the handles of the pliers, the legs 349b may be bent together to release the clip 349 from the cavity member groove 351 or alternatively to insert the clip 349 into the groove 351.

It will, of course, be understood that modifications of the present invention, in its various aspects, will be apparent to those skilled in the art, some being apparent only after study, others being matters of routine mechanical and electronic design. Other embodiments are also possible, their specific designs depending upon the particular application. As such, the scope of the invention should not be limited by the particular embodiments herein described but should be defined only by the appended claims and equivalents thereof.

What is claimed is:

1. A motor for a medication pump, comprising:
   an energizable winding having a length and defining a magnetic field generation area adjacent said winding wherein a magnetic field is generated in said magnetic field generation area in response to energizing said winding;
   a housing comprising a first member having a guide track, said housing further having a unitary, second member defining a cavity adapted to receive said winding, said housing cavity having a length at least as long as said winding length, said housing second member further having an opening at one end and adapted to receive said housing first member wherein said first member guide track extends at least partially into said winding magnetic field generation area, said housing second member further having a guide track aligned with the first member guide track;
   an armature slidingly received in said housing first member guide track, said armature being adapted to slide along said first member guide track in response to a magnetic field generated in said magnetic field generation area;
   a push member slidingly received in said housing second member guide track and positioned to be engaged by said armature and to slide along said second member guide track in response to engagement by said armature; and
   a pawn having a base at one end thereof and a tip projecting from said base at an opposite end thereof, said pawn being mounted in said housing and adapted for rocking motion between a rest position and an actuated position, said pawn base being positioned to be engaged by said push member and moved from said rest position to said engaged position in response to engagement of said pawn by said push member.

2. The motor of claim 1, wherein said housing second member further has a guide track aligned with the first member armature guide track, said motor further comprising a push member slidingly received in said housing second member guide track and positioned to be engaged by said armature and to slide along said second member guide track in response to engagement by said armature.

3. The motor of claim 2, further comprising: a pawn having a base at one end thereof and a tip projecting from said base at an opposite end thereof, said pawn being mounted in said housing and adapted for rocking motion between a rest position and an actuated position, said pawn base being positioned to be engaged by said push member and moved from said rest position to said engaged position in response to engagement of said pawn by said push member.

4. The motor of claim 1, wherein said armature has an engagement face and said push member has an engagement face positioned to be engaged by said armature engagement face, wherein the width of said push member engagement face is at least 40% of the width of said armature engagement face.

5. The motor of claim 1, wherein said push member is a unitary body formed of a nonmagnetically permeable material.

6. The motor of claim 1, wherein said housing second member further defines a bushing having an aperture and wherein said tip of said pawn is positioned to extend through said bushing aperture to the exterior of said housing.

7. The motor of claim 1, wherein said winding defines a cylindrically shaped interior and said push member guide track and said armature guide track are coaxially aligned with said winding interior.

8. A motor for a medication pump, comprising:
   an energizable winding having a length and defining a magnetic field generation area adjacent said winding wherein a magnetic field is generated in said magnetic field generation area in response to energizing said winding;
   a housing comprising a first member having a guide track, said housing further having a unitary, second member defining a cavity adapted to receive said winding, said housing cavity having a length at least as long as said winding length, said housing second member further having an opening at one end and adapted to receive said housing first member wherein said first member guide track extends at least partially into said winding magnetic field generation area, said housing second member further having a guide track aligned with the first member guide track;
   an armature slidingly received in said housing first member guide track, said armature being adapted to slide along said first member guide track in response to a magnetic field generated in said magnetic field generation area; and
   a push member slidingly received in said housing second member guide track and positioned to be engaged by said armature and to slide along said second member guide track in response to engagement by said armature, wherein said armature has an engagement face and said push member has an engagement face positioned to be engaged by said armature engagement face, wherein the width of said push member engagement face is at least 40% of the width of said armature engagement face, and wherein the area of said push member engagement face is approximately 41% of the area of said armature engagement face.

9. A motor for a medication pump, comprising:

an energizable winding having a length and defining a magnetic field generation area adjacent said winding wherein a magnetic field is generated in said magnetic field generation area in response to energizing said winding;

a housing comprising a first member having a guide track, said housing further having a unitary, second member defining a cavity adapted to receive said winding, said housing cavity having a length at least as long as said winding length, said housing second member further having an opening at on end and adapted to receive said housing first member wherein said first member guide track extends at least partially into said winding magnetic field generation area, said housing second member further having a guide track aligned with the first member guide track;

an armature slidingly received in said housing first member guide track, said armature being adapted to slide long said first member guide track in response to a magnetic field generated in said magnetic field generation area; and a push member slidingly received in said housing second member guide track and positioned to be engage by said armature and to slide along said second member guide track in response to engagement by said armature, wherein said armature has a stem portion which is slidingly received in said first member guide track and a head portion which has an engagement face positioned to engage said push member, wherein said armature head portion is wider than said armature stem portion and has a length equal to at least 10% of said winding length.

10. The motor of claim 9, wherein said armature head portion has a length which is approximately 20% of said winding length.

11. A motor for a medication pump, comprising:

an energizable winding having a length and defining a magnetic field generation area adjacent said winding wherein a magnetic field is generated in said magnetic field generation area in response to energizing said winding;

a housing comprising a first member having a guide track, said housing further having a unitary, second member defining a cavity adapted to receive said winding, said housing cavity having a length at least as long as said winding length, said housing second member further having an opening at one end and adapted to receive said housing first member wherein said first member guide track extends at least partially into said winding magnetic field generation area, said housing second member further having a guide track aligned with the first member guide track;

an armature slidingly received in said housing first member guide track, said armature being adapted to slide along said first member guide track in response to a magnetic field generated in said magnetic field generation area; and a push member slidingly received in said housing second member guide track and positioned to be engaged by said armature and to slide along said second member guide track in response to engagement by said armature, wherein said armature has a stem portion which is slidingly received in said first member guide track and a head portion which has an engagement face positioned to engage said push member wherein said armature head portion has a cross-sectional area between 35 and 63% larger than the cross-sectional area of said armature stem portion.

12. The motor of claim 11, wherein said armature head portion has a cross-sectional area which is approximately 45% larger than the cross-sectional area of said armature stem portion.

13. A motor for a medication pump, comprising:

an energizable winding having a length and defining a magnetic field generation area adjacent said winding wherein a magnetic field is generated in said magnetic field generation area in response to energizing said winding;

a housing comprising a first member having a guide track, said housing further having a unitary, second member defining a cavity adapted to receive said winding, said housing cavity having a length at least as long as said winding length, said housing second member further having an opening at one end and adapted to receive said housing first member wherein said first member guide track extends at least partially into said winding magnetic field generation area, said housing second member further having a guide track aligned with the first member guide track;

an armature slidingly received in said housing first member guide track, said armature being adapted to slide along said first member guide track in response to a magnetic field generated in said magnetic field generation area; and a push member slidingly received in said housing second member guide track and positioned to be engaged by said armature and to slide along said second member guide track in response to engagement by said armature, wherein said armature stem portion has an engagement surface and said first member guide track has an engagement surface positioned to engage said armature stem portion engagement surface and each engagement surface has a surface roughness of 8–12 microns.

14. A motor for a medication pump, comprising:

an energizable winding having a length and defining a magnetic field generation area adjacent said winding wherein a magnetic field is generated in said magnetic field generation area in response to energizing said winding;

a housing comprising a first member having a guide track, said housing further having a unitary, second member defining a cavity adapted to receive said winding, said housing cavity having a length at least as long as said winding length, said housing second member further having an opening at one end and adapted to receive said housing first member wherein said first member guide track extends at least partially into said winding magnetic field generation area, said housing second member further having a guide track aligned with the first member guide track;

an armature slidingly received in said housing first member guide track, said armature being adapted to slide along said first member guide track in response to a magnetic field generated in said magnetic field generation area; and a push member slidingly received in said housing second member guide track and positioned to be engaged by said armature and to slide along said second member guide track in response to engagement by said armature, wherein said armature has an engagement face and said push member has an engagement face positioned to be engaged by said armature engagement face, wherein the width of said push member engagement face is at least 40% of the width of said armature engagement face, wherein said push member has a single diameter cylindrical shape and said second member guide track for said push member has a single diameter cylindrical shape sized to slidingly receive said push member.

15. A portable infusion pump adapted to be carried on the body of a user, comprising:

a portable housing;

a dispenser positioned within said housing and having a reservoir adapted to store fluid medication; and a motor coupled to said dispenser and adapted to actuate said dispenser to dispense said fluid medication when activated; said motor comprising:

an energizable, annular shaped winding having a length and defining a magnetic field generation area aligned with a central axis of said winding, wherein a magnetic field is generated in said magnetic field generation area in response to energizing said winding;

a motor housing comprising an end cap member having a guide track, said motor housing further having a unitary, cavity member defining a cavity adapted to receive said winding, said motor housing cavity having a length at least as long as said winding length, said motor housing cavity member further having an opening at one end and adapted to receive said motor housing end cap member, wherein said end cap member guide track extends at least partially into said winding magnetic field generation area; and an armature slidingly received in said motor housing end cap guide track, said armature being adapted to slide along said end cap guide track in response to a magnetic field generated in said magnetic field generation area.

16. The pump of claim 15, wherein said housing second member further has a guide track aligned with the first member armature guide track, said motor further comprising a push member slidingly received in said housing second member guide track and positioned to be engaged by said armature and to slide along said second member guide track in response to engagement by said armature.

17. The pump of claim 16, wherein said armature has an engagement face and said push member has an engagement face positioned to be engaged by said armature engagement face wherein the width of said push member engagement face is at least 40% of the width of said armature engagement face.

18. The pump of claim 17, wherein the area of said push member engagement face is approximately 41% of the area of said armature engagement face.

19. The pump of claim 17, wherein said armature has a stem portion which is slidingly received in said first member guide track and a head portion which has an engagement face positioned to engage said push member wherein said armature head portion is wider than said armature stem portion and has a length at least 10% of said winding length.

20. The pump of claim 19, wherein said armature head portion has a length which is approximately 20% of said winding length.

21. The pump of claim 16, wherein said armature has a stem portion which is slidingly received in said first member guide track and a head portion which has an engagement face positioned to engage said push member wherein said armature head portion has a cross-sectional area between 35 and 63% larger than the cross-sectional area of said armature stem portion.

22. The pump of claim 21, wherein said armature head portion has a cross-sectional area which is approximately 45% larger than the cross-sectional area of said armature stem portion.

23. The pump of claim 16, wherein said armature stem portion has an engagement surface and said first member guide track has an engagement surface positioned to engage said armature stem portion engagement surface and each engagement surface has a surface roughness of less than 16 microns.

24. The pump of claim 16, wherein said push member is a unitary body formed of a nonmagnetically permeable material.

25. The pump of claim 16, wherein said push member has a single diameter cylindrical shape and said second member guide track for said push member has a single diameter cylindrical shape sized to slidingly receive said push member.

26. The pump of claim 16, further comprising a pawn having a base at one end thereof and a tip projecting from said base at an opposite end thereof, said pawn being mounted in said housing and adapted for rocking motion between a rest position and an actuated position, said pawn base being positioned to be engaged by said push member and moved from said rest position to said engaged position in response to engagement of said pawn by said push member.

27. The pump of claim 26, wherein said housing second member further defines a bushing having an aperture and wherein said tip of said pawn is positioned to extend through said bushing aperture to the exterior of said housing.

28. The pump of claim 26, wherein said winding defines a cylindrically shaped interior and said push member guide track and said armature guide track are coaxially aligned with said winding interior.

29. The pump of claim 15 wherein said armature has a length which is 65% of the length of said winding.

30. The pump of claim 15 wherein said armature has a length greater than 0.300 inches.

31. The pump of claim 30 wherein said armature has a length of 0.350 inches.

* * * * *